US008766182B2

(12) United States Patent
Yamazaki et al.

(10) Patent No.: US 8,766,182 B2
(45) Date of Patent: *Jul. 1, 2014

(54) METHOD FOR DETECTING INFORMATION OF AN ELECTRIC POTENTIAL ON A SAMPLE AND CHARGED PARTICLE BEAM APPARATUS (71) Applicant: Hitachi High-Technologies Corporation, Tokyo (JP)

(72) Inventors: Minoru Yamazaki, Hitachinaka (JP); Akira Ikegami, Hitachinaka (JP); Hideyuki Kazumi, Hitachinaka (JP); Osamu Nasu, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/924,213

(22) Filed: Jun. 21, 2013

(65) Prior Publication Data
US 2013/0284921 A1 Oct. 31, 2013

Related U.S. Application Data (63) Continuation of application No. 13/568,922, filed on Aug. 7, 2012, now Pat. No. 8,487,250, which is a continuation of application No. 11/958,625, filed on Dec. 18, 2007, now Pat. No. 8,263,934.

(30) Foreign Application Priority Data

Dec. 19, 2006 (JP) ................... 2006-340650

(51) Int. Cl.
*H01J 37/26* (2006.01)
(52) U.S. Cl.
USPC .......... 250/307; 250/305; 250/306; 250/309; 250/310; 250/311; 324/76.11; 324/500; 324/501

(58) Field of Classification Search
USPC ............ 250/306, 307, 309, 310, 311, 396 R, 250/397; 324/71.1, 76.11, 500, 501
See application file for complete search history.

(56) References Cited

U.S. PATENT DOCUMENTS 5,006,795 A  4/1991  Yoshizawa et al.
6,521,891 B1  2/2003  Dotan et al.
(Continued)

FOREIGN PATENT DOCUMENTS

JP  1-214769 A  8/1989
JP  4-229541 A  8/1992
(Continued)

OTHER PUBLICATIONS http://www.thefreedictionary.com/energy+level.
(Continued)

*Primary Examiner* — Nicole Ippolito
(74) *Attorney, Agent, or Firm* — Crowell & Moring LLP (57) ABSTRACT An object of the present invention is to provide a method and apparatus for measuring a potential on a surface of a sample using a charged particle beam while restraining a change in the potential on the sample induced by the charged particle beam application, or detecting a compensation value for a change in a condition for the apparatus caused by the sample being electrically charged. In order to achieve the above object, the present invention provides a method and apparatus for applying a voltage to a sample so that a charged particle beam does not reach the sample (hereinafter, this may be referred to as "mirror state") in a state in which the charged particle beam is applied toward the sample, and detecting information relating to a potential on the sample using signals obtained by that voltage application.

8 Claims, 8 Drawing Sheets

(56) References Cited

U.S. PATENT DOCUMENTS

| | | |
|---|---|---|
| 6,563,114 B1 | 5/2003 | Nagahama et al. |
| 6,967,328 B2 | 11/2005 | Kienzie et al. |
| 7,239,148 B2 | 7/2007 | Suhara |
| 7,544,937 B2 | 6/2009 | Frosien |
| 7,982,188 B2 | 7/2011 | Shinada et al. |
| 7,989,768 B2 | 8/2011 | Ikegami et al. |
| 8,263,934 B2* | 9/2012 | Yamazaki et al. ............ 250/307 |
| 2005/0263715 A1 | 12/2005 | Nakasuji et al. |
| 2006/0011835 A1* | 1/2006 | Murakoshi et al. ........... 250/310 |
| 2006/0226360 A1 | 10/2006 | Frosien |
| 2007/0040118 A1 | 2/2007 | Cheng et al. |
| 2007/0138388 A1* | 6/2007 | Ward et al. .................... 250/288 |

FOREIGN PATENT DOCUMENTS

| | | |
|---|---|---|
| JP | 10-125271 A | 5/1998 |
| JP | 2001-236915 A | 8/2001 |
| JP | 2004-14485 A | 1/2004 |
| JP | 2004-134374 A | 4/2004 |
| JP | 2005-166542 A | 6/2005 |
| JP | 2005-345272 A | 12/2005 |
| JP | 2005-347281 A | 12/2005 |
| JP | 2006-260957 A | 9/2006 |
| JP | 2006-278329 A | 10/2006 |

OTHER PUBLICATIONS

Bureau International des Poids et Mesures, "Non-SI units accepted for use with the SI, and units based on fundamental constants," available at http://www1.bipm.org/en/si/si_brochure/chapter4/table7.html (last accessed Jul. 11, 2011).

Japanese Office Action dated Oct. 4, 2011 (three (3) pages).

Japanese Office Action dated Mar. 25, 2013 (Two (2) pages).

* cited by examiner

METHOD FOR DETECTING INFORMATION OF AN ELECTRIC POTENTIAL ON A SAMPLE AND CHARGED PARTICLE BEAM APPARATUS

CROSS REFERENCE TO RELATED APPLICATION

This application is a continuation of U.S. application Ser. No. 13/568,922, filed on Aug. 7, 2012, which is a continuation of U.S. application Ser. No. 11/958,625, filed on Dec. 18, 2007, which claims priority from Japanese Patent Application No. 2006-340650, filed on Dec. 19, 2006 in the Japanese Patent Office, the entire disclosures of which are incorporated by reference herein.

BACKGROUND OF THE INVENTION

1. Field of the Invention

The present invention relates to a charged particle beam irradiation method for applying a charged particle beam to a sample, and to a charged particle beam apparatus. In particular, the invention provides a method for detecting information concerning an electric potential on a sample, which is preferable for measuring an electric potential on a sample, and a charged particle beam apparatus for detecting an electric potential on a sample.

2. Background Art

Recently, with the advancement of semiconductor devices, the importance of semiconductor measurement and test technology has been increasing. A scanning electron microscope, which is typified by a CD-SEM (Critical Dimension-Scanning Electron Microscope), is an apparatus for measuring a pattern formed on a semiconductor device by scanning a sample with an electron beam, and detecting electrons (such as secondary electrons) emitted from the sample. In such apparatus, it is necessary to set proper apparatus conditions to perform highly-accurate measurements and tests. Some samples of recent devices become electrically charged due to electron beam irradiation or the influence of semiconductor processing. More specifically, insulating samples, such as a resist, an insulating film or a low-k material, are known to be easily charged.

When a sample is electrically charged, the electron orbit is distorted, which may cause astigmatism or image blurring. JP Patent Publication (Kokai) No. 4-229541 (Patent Document 1), JP Patent Publication (Kokai) No. 10-125271 (Patent Document 2), and JP Patent Publication (Kokai) No. 2001-236915 (Patent Document 3) each describe a technique for measuring the charge quantity on such an electrically charged sample and controlling a voltage applied to the sample so as eliminate the influence of the charge in order to properly perform focusing on the sample.

Also, JP Patent Publication (Kokai) No. 1-214769 (Patent Document 4) describes a technique for detecting field emission current emitted from a metal needle with a sharp tip or tunnel current in order to contactlessly measure the potential on a sample.

SUMMARY OF THE INVENTION

Each of the techniques described in the above Patent Documents 1 to 3 relates to a technique for measuring a charge quantity on a sample and adjusting the conditions for the apparatus based on the measurement. However, the charge quantity is measured by detecting a signal obtained by applying an electron beam to the sample, so further charging may be induced due to the electron beam application. As a result, it is difficult to measure the charge quantity before the electron beam application.

Meanwhile, with the technique described in Patent Document 4, it is possible to measure an electric potential on a surface of a sample without charge being induced by an electron beam, but the technique has problems in the potential on the sample changing due to the metal needle approaching the sample, and in discharging when the charge quantity is large.

An object of the present invention is to provide a method and apparatus for measuring an electric potential on a surface of a sample using a charged particle beam while mitigating a change in the potential on the sample induced by the charged particle beam application, or detecting a compensation value for a change in a condition for the apparatus caused by the sample being electrically charged.

In order to achieve the above object, the present invention provides a method and apparatus for applying a voltage to a sample, such that a charged particle beam does not reach the sample (hereinafter, this may be referred to as "mirror state") when the charged particle beam is applied toward the sample, and detecting information relating to a potential on the sample using a signal obtained as a result of that voltage application.

One preferred embodiment of the present invention provides a method and apparatus for detecting information of an electric potential on a sample, comprising detecting information relating to an electric potential on a sample based on a difference between information obtained based on charged particles detected when a voltage that corresponds to an energy higher than acceleration energy of a charged particle beam emitted from a charged particle source is applied to the sample and information obtained based on charged particles at a predetermined electric potential on the sample when the charged particle beam is applied from the charged particle source toward the sample.

In the above-described arrangement, a potential on a sample or adjustment conditions for the apparatus are detected from information obtained in a state in which a charged particle beam is not applied to the sample, and accordingly it is possible to detect the potential on the sample, etc., while restraining a change in the potential on the sample.

DETAILED DESCRIPTION OF THE PREFERRED EMBODIMENTS

Recently, miniaturization or high-density integration of Ultra Large Scale Integrated (ULSI) devices has progressed rapidly, and device processing with a processing size of several tens of nanometers has been growing. Multilayering using various kinds of new materials such as a low-dielectric-constant film or a metal gate film for speed-up, and a three-layer resist for enhancing resistance to etching, has been increasingly employed. Consequently, the demands for critical dimension (CD) control during ULSI device processing have become strict.

Insulating materials, such as resists, insulating films, and low-k materials are often used in semiconductor processing, but the surface of such an insulating material is electrically charged by electron beam application. The charged material may change the quantity of secondary electrons that are getting out of the sample surface, or distort the orbit of a primary electron beam, resulting in the scanning electron microscope image being distorted. Consequently, it becomes difficult to measure the true processing size or shape. In the case of an ArF resist, for example, whether line-edge roughness (LER) has occurred during etching, or a size measurement error has arisen in the electron microscope due to charging cannot be judged. Also, in high-aspect contact hole observation, a problem may arise in that the shape of a contact hole is observed as being distorted, or in that it becomes difficult to distinguish between the upper diameter and the lower diameter of a hole.

Charge changes spatially/temporally, the changes including attenuation due to hole-electron recombination, in addition to spatial changes due to movement and diffusion of electrons. Also, a sample surface is positively or negatively charged depending on the energy of electrons falling on the sample surface. Accordingly, controlling such charging has become important. As a result of the electron orbit being distorted by charging, a part that cannot form an image (astigmatism) or image blurring may occur. A function that collects electrons at a predetermined position to automatically perform focusing (auto-focusing function) may also have problems, such as displacement from the initial focus position, due to the charging, taking more time to perform focusing. So it has become important to know the size and distribution of the charge potential.

Hereinafter, preferred embodiments of the present invention will be described with reference to the drawings.

Figure 1:
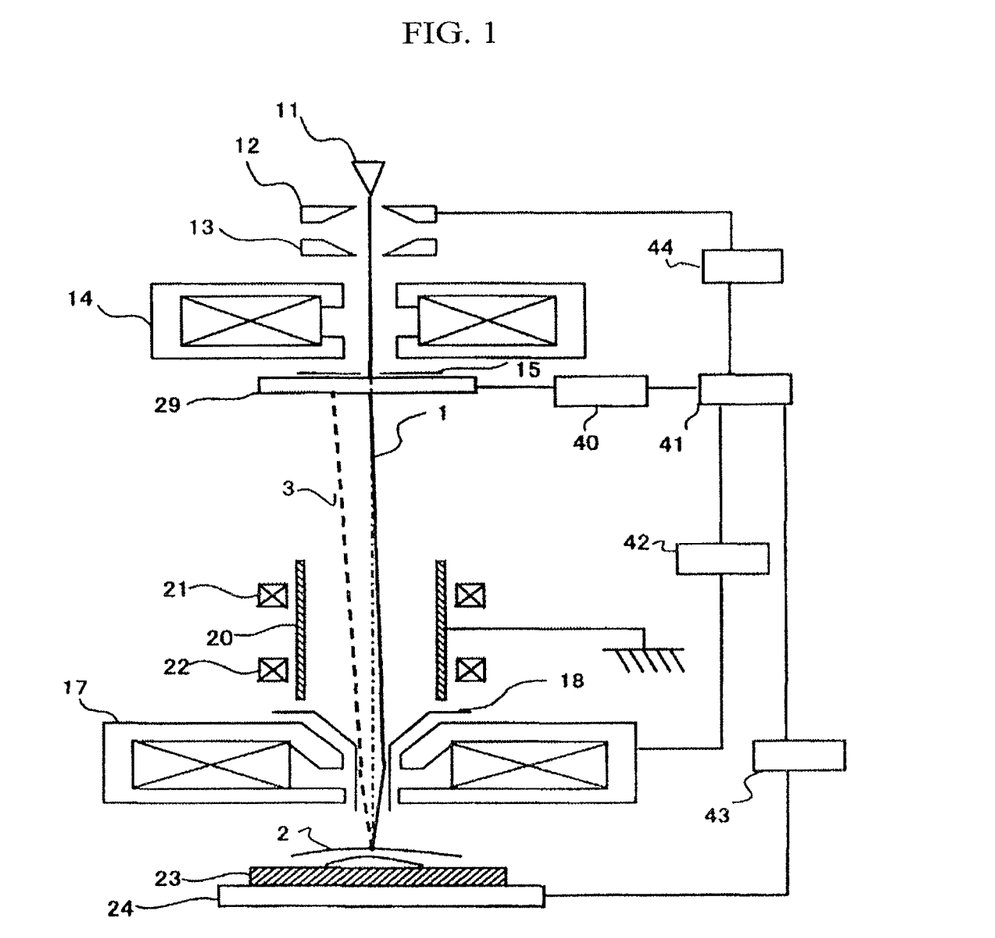
FIG. 1 is a diagram schematically illustrating a scanning electron microscope.

FIG. 1 is a diagram schematically illustrating a scanning electron microscope. In the below description, a scanning electron microscope in which a sample is scanned with an electron beam (Scanning Electron Microscope: SEM) will be described as an example, but the present invention is not limited to this example, and can be employed in another particle beam apparatus, such as a FIB(Focused Ion beam) apparatus. However, it is necessary to change the polarity of a voltage applied to the sample according to the polarity of the charge of the beam. Also, FIG. 1 merely shows an example of a scanning electron microscope, and the present invention can be employed in a scanning electron microscope having a configuration different from that shown in FIG. 1 as far as such employment does not change the gist of the preset invention.

In the scanning electron microscope shown in FIG. 1, an extraction voltage is applied between a field emission cathode 11 and an extractor electrode 12, and a primary electron beam is thereby extracted.

The thus-extracted primary electron beam 1 is accelerated by an acceleration electrode 13, and is focused by a condenser lens 14, and is subject to a scanning deflection by an upper scan deflector 21 and a lower scan deflector 22. The deflection intensities of upper scan deflector 21 and the lower scan deflector 22 are adjusted so that two-dimensional scanning on a sample 23 is carried out with the center of an objective lens 17 set as a supporting point.

The deflected primary beam 1 is further accelerated by a post-acceleration voltage 19 in an acceleration cylinder 18 provided in a passageway in the objective lens 17. The primary electron beam 1 that has been subjected to post-acceleration is focused by the effect of the objective lens 17. A tubular cylinder 20 is grounded, forming an electric field accelerating the primary electron beam 1 between the tubular cylinder 20 and the acceleration cylinder 18.

Electrons emitted from the sample, such as secondary electrons or backscattered electrons, are accelerated in a direction opposite the direction in which the primary electron beam 1 is applied, by an electric field formed between a negative voltage applied to the sample (hereinafter, this may be referred to as "retarding voltage"), and the acceleration cylinder 18, and detected by a detector 29.

The electrons detected by the detector 29 are displayed on an image display (not shown) in synchronization with scan signals supplied to the scan deflectors. Also, the obtained image is stored in frame memory (not shown). Current or voltage supplied or applied to the components of the scanning electron microscope shown in FIG. 1 may be controlled using a controller provided separately from the scanning electron microscope body.

Embodiment 1

Hereinafter, a method for measuring a potential on a sample using an electron beam, and an apparatus for implementing that method will be described.

The acceleration energy of electrons Ee is determined by the difference in potential between the field emission cathode 11 and the acceleration electrode 13.

First, assume that the acceleration energy of electrons is Ee and that a potential on a sample Vr, |−Vr| is set to a value corresponding to an energy greater than Ee. When an electron beam is emitted toward the sample in this state, the incident electrons do not fall on the sample and are reflected at a position immediately above the sample (these electrons are referred to as "mirror electrons"). The reflected mirror electrons move in the opposite direction in the lens system. A detector is provided in the lens system to detect the position where the mirror electrons have arrived, thereby detecting the difference or "displacement" between the position where incident electrons have passed (the "object point") and the position where the mirror electrons have arrived. (See FIG. 11.) Without the sample charging, the electrons would be reflected following the same orbit as that of the incident electrons, so this displacement quantity reflects the value of the sample potential Vr. Accordingly, the potential on the sample can be measured by measuring the relationship between the displacement quantity and Vr in advance. (See FIG. 11.)

The "displacement" (difference) in this embodiment can be obtained by detecting the spread or a change in the positions of mirror electrons projected onto the detector, or a two-dimensional displacement of an image formed by the mirror electrons. A potential on the sample can also be obtained by detecting the rotation between images or the difference in image blurring between images.

The relationship between the displacement quantity and the potential on the sample can be obtained as follows, for example. The position of the object point is assumed to be Zc when the sample height is Z and the potential on the sample is Vr1, and a focused state is created in this state by adjusting the parameters for the lens system.

Here, it is assumed that the detector is located at a position z1 in the height direction, and that the mirror electron detection position at that time is Zr1 (x1, y1, z1). This is used as a reference value. Next, setting the potential on the sample to be Vr2, and a beam with the same energy as Vr2 is applied, and the position Zr2 (x2, y2, z1) where the mirror electrons have arrived at that time is obtained by the detector. The displacement quantity between Zr1 and Zr2 is obtained and then a Vr-Zr correlation curve representing the correlation between that difference and the potential is obtained. At this time, as the number of combinations of data (Vr and Zr) increases, a correlation curve with higher accuracy can be obtained. In this state, supposing that the position where the mirror electrons have arrived when the charged sample is observed is Zr3, the potential on the sample can be calculated from the Vr-Zr correlation curve. The electron beam does not fall on the sample, so the charge potential can be measured without changing the state of the sample.

Here, Vr has been changed as a method for obtaining a correlation curve, but there are other methods. For example, if the objective lens is formed of a magnetic field coil, the relationship between the image surface position Z and exciting current Ic exciting the objective lens can be considered as being known, so by measuring Zr1 of the mirror electrons at the reference value alone, a charge state Vr3 can be estimated from a change in displacement when the exciting current is changed. Besides this, the Vr-Zr correlation curve can also be obtained by changing the sample height, a booster voltage Vb, the position of the object point for the primary electrons relative to the objective lens, or other parameters.

When detecting the spread or displacement of a beam projected in a detector, it is desirable to use a detector with a plurality of detection elements spread in two dimensions. As a result of obtaining the position where the mirror electrons have arrived or the distribution of the mirror electrons from output signals from the plurality of detection elements, a displacement from the reference value can be obtained.

Also, a displacement quantity can be detected more easily by detecting the displacement quantity using images. The mirror electrons are reflected at a position immediately above the sample, and are subjected to the influence of the beam passageway and structures during passing through the lens system. In order to obtain an image, a scanning incident beam may be moved over the region. As a result, the shapes of the structures in the beam passageway appear in an image.

Furthermore, when detecting an image rotation, the quantity of rotation of a structure displayed in a projected image is monitored. More specifically, there are methods in which a potential on a sample is obtained from a rotation angle when exciting current is changed and focusing is made on a structure under reference mirror conditions, and in which a potential on a sample is obtained from the change quantity ($d\theta/dI_{obj}$) of a rotation angle when existing current has been changed from reference conditions. Although the relationship between the exciting current for the objective lens and the rotation angle has been described above, the potential on the sample can be measured even though the exciting current may be replaced with a parameter relating to optical conditions during mirroring, such as the potential on the sample Vr, the primary electron object point position, the booster voltage or the sample height. Also, it is desirable that a structure has an asymmetric shape such as a single arrow or a character "F".

Furthermore, if the correlation between the rotation quantity and the sample potential is obtained and the potential on the sample is estimated from the rotation quantities under a plurality of conditions obtained by the monitoring, the potential on the sample can be measured more accurately. Also, since the focus of the electron beam is changed as a result of adjusting the voltage applied to the sample, the potential on the sample according to the degree of image blurring can be detected if the correlation between the degree of the image blurring and the potential on the sample. The blurring can be detected by directly measuring the beam distribution of a detection-target surface (method 1), or using edge drooping of a structure having the same level of size as a spot diameter on the detection-target surface (method 2), by means of a plurality of detectors being two-dimensionally provided. If method 2 is used, the blurring quantity for a broad range can be measured with high accuracy if structures of different sizes are placed.

As described above, the potential on the sample can be measured by monitoring the rotation quantity, blurring, magnification ratio, image distortion or composite information of these, etc.

Hereinafter, a preferred embodiment for measuring a potential on a sample will be described with reference to the drawings.

Here, it is assumed that a sample 23 is electrically charged to have a certain potential. A potential Vr is provided to the sample by means of a stage voltage control system 43. Here, Vr is provided so that it corresponds to an energy that is sufficiently greater than acceleration energy Ee of electrons. The acceleration energy Ee mentioned here refers to a value before deceleration by the voltage applied to the sample. For example, when Ee is 2 keV, Vr greater than around −2200 V is provided. The quantity of charge on the sample can be considered to be from minus several hundreds V to around plus 200 V at maximum, so it is sufficient that the absolute value is greater than −2200 V. In those cases, an equipotential surface 2 of −2000 V is formed at a position above the sample. This potential surface is referred to as a mirror surface, and the primary electron beam is reflected on this surface and returns upward.

These electrons are here referred to as mirror electrons 3. The mirror electrons 3 that have passed the lens system reach the detector 29, which detects the position Zr3 (x3, y3, zr) of the mirror electrons 3. Here, zr is a position in the height direction. A computing unit 40 calculates a "displacement" of this Zr3 information from the predetermined reference value Zr1, and then calculates the charge potential Vr3 on the sample from this "displacement" quantity based on the "correlation curve between the mirror electron position and the potential". This information is sent to an analyzer 41, and in order to control the charge state, the analyzer 41 sets signals for control system parameters. Examples of the control system include an objective lens control system 42, the stage voltage control system 43 and an acceleration voltage control system 44, which set existing currents, a stage voltage, and extraction/acceleration energy of electrons, respectively, thereby controlling the charge state.

Figure 11:
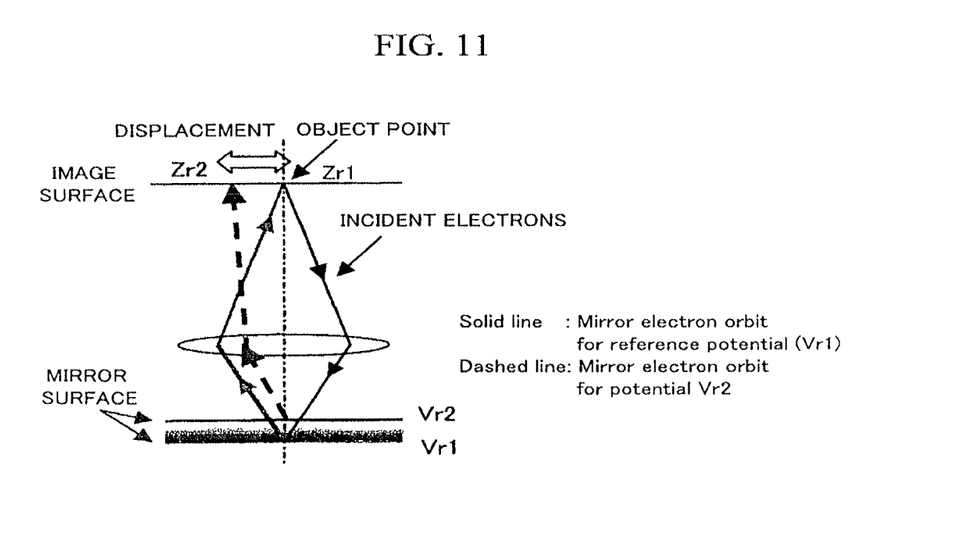
FIG. 11 is a diagram illustrating the principle of potential measurement using mirror electrons.

The relationship between the displacement quantity and the potential on the sample can be obtained as follows, for example. The position of the object point is assumed to be Zc when the sample height is Z and the potential on the sample is Vr1, and a focused state is created in this state by adjusting the parameters for the lens system. It is assumed that the detector is located at a position z1 in the height direction. As shown in FIG. 11, the mirror electron detection position at that time is assumed to be Zr1 (x1, y1, z1). This is used as a reference value. At this time, it is better to use a conductor or semiconductor sample that does not bear electric charge for the sample. Next, the potential on the sample is set to Vr2, and a beam with the same energy as Vr2 is emitted and the position Zr2 (x2, y2, z1) where the mirror electrons have arrived at this time is obtained from the detector.

The displacement quantity between Zr1 and Zr2 is calculated and then the Vr-Zr correlation curve representing the correlation between this displacement and the potential is obtained. At that time, as the number of data combinations (Vr and Zr) is greater, a more accurate correlation curve can be obtained. Supposing that the position where the mirror electrons have arrived when the charged sample is observed in this state is Zr3, the potential on the sample can be obtained from the Vr-Zr correlation curve.

An image at the above-mentioned reference value is set to 51, and is used as a reference image. Also, an image when the potential has been changed to the sample potential Vr2 is acquired as a reference image, and a Vr-S correlation curve is prepared. In this state, image signals at a measurement target sample are detected by means of the detector, and the image S3 is compared with the above-mentioned reference images, thereby calculating the charge potential Vr3.

When a displacement from an incident position is detected using images, as described above, various detection image objects can be considered depending on the scanning electron microscope configuration.

For example, the position of a hole or a structure, or the blurring degree of an image of a hole or a structure is obtained from the quantity of change in contrast of an edge portion of the hole or the structure. Other possible approaches may include: obtaining the blurring degree of a hole or a structure from its change in area; detecting a rotation angle from a reference image of a hole or a structure; and checking the luminance of the entire image.

Beside the lens system, a structure, such as a reflecting plate (in the description of this embodiment, this is an electrode for electrons accelerated by a retarding voltage to collide and secondary electrons generated are detected by a separately-provided secondary electron detector) or a mesh, may also be used as a target, or something that can be used as a mark, for example, a hole with a triangular or multi-angular shape for reference, or an arrow mark in a lens system, may be placed intentionally.

In the following embodiment, another method for detecting displacement will be described in detail.

Embodiment 2

Figure 2:
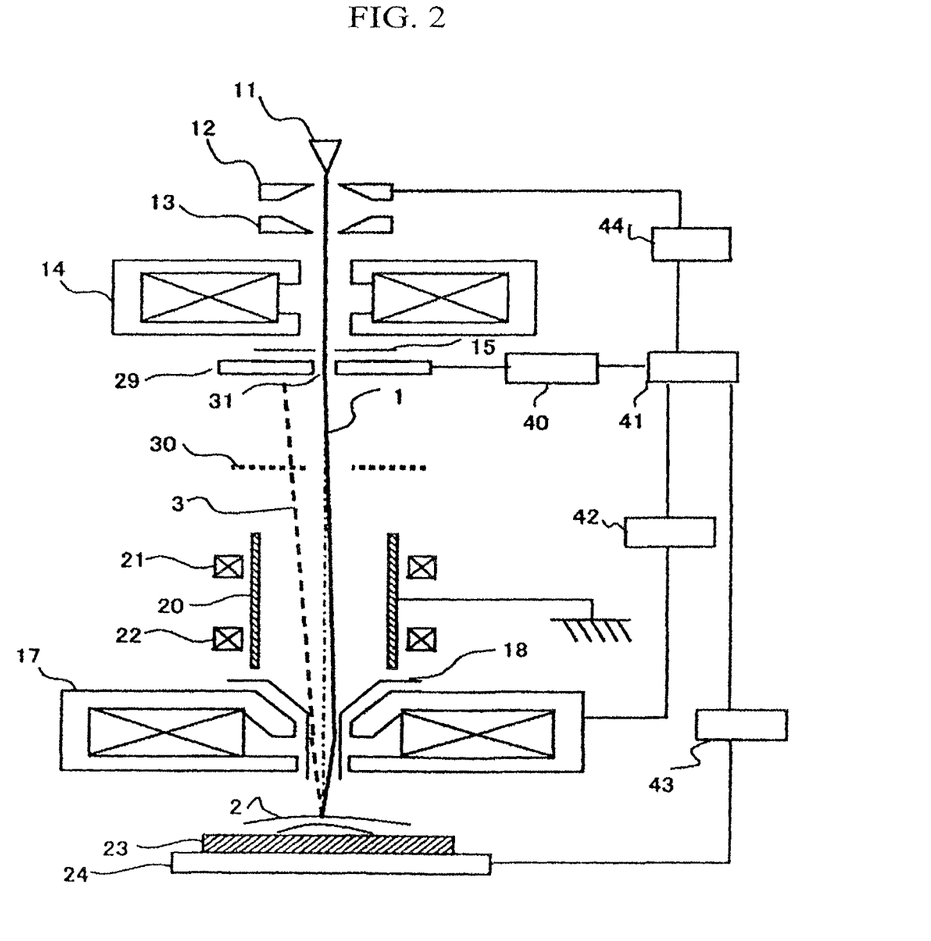
FIG. 2 is a diagram illustrating another scanning electron microscope configuration.

FIG. 2 is a diagram for describing a second embodiment for detecting a potential on a sample. A primary electron beam 1 that has been focused by a condenser lens 14 and has passed a diaphragm 15 is deflected using an upper scan deflector 21 and a lower scan deflector 22.

At this time, as in embodiment 1 above, a potential applied to the sample is set so that the absolute value of the potential on the sample is greater than the acceleration energy of the primary electron beam 1 during passing through an objective lens 17. The primary electron beam 1, which does not reach a sample 23, is reflected on a mirror surface 2 and returns toward a detector 29 as mirror electrons 3. As a result of deflecting the primary electron beam 1 by means of the upper scan deflector 21 and the lower scan deflector 22, the orbit of the mirror electrons 3 returning is also changed, so when the mirror electrons 3 are detected by the detector 29 and imaged by a computing unit 40, the shape of a hole or structure that the mirror electrons have passed through is reflected on the image.

Figure 3:
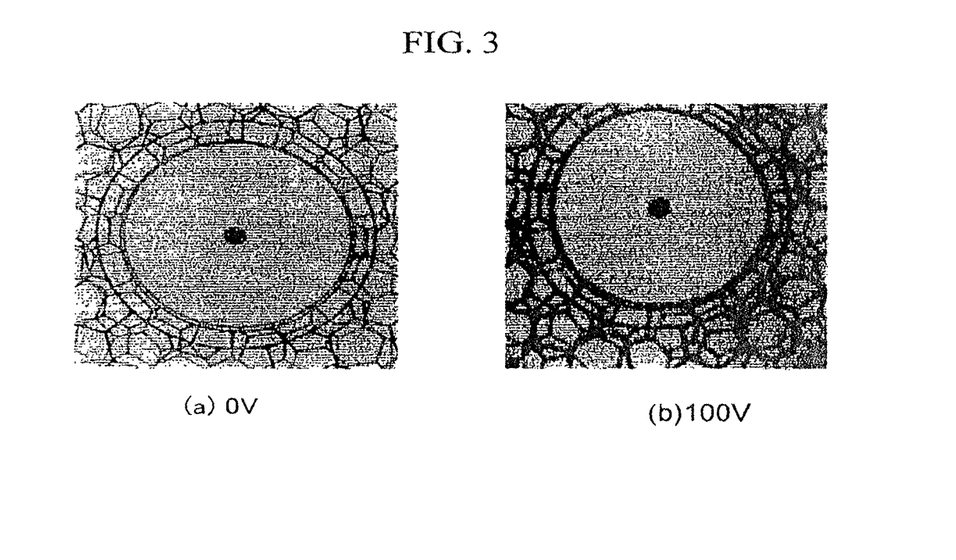
FIGS. 3A and 3B are diagrams indicating a change in an image formed by mirror electrons according to the potential of its electric charge.

For example, when a mesh 30 (constituting an energy filter) is placed in the lens system and when a beam transmission aperture 31 is provided in the detector 29, an image in which a mesh or a hole appears, like FIGS. 3A and 3B, can be obtained as a result of the mirror electrons 3 passing through the transmission aperture 31.

FIG. 3A shows a state in which the charge potential when a charge potential on a sample is 0. Charge potential is defined as charge potential=potential on the sample−potential set on the sample.

In other words, FIG. 3A shows an image when the sample is not electrically charged, and FIG. 3B shows an image when the charge potential is 100 V. FIG. 3A shows that when the potential is changed or changes, the hole position at the center part and the shadow part of the mesh are moved. These images are registered in advance in the computing unit 40 as images with their potentials known (reference images).

Next, an image of the mirror electrons 3 by a sample 23 with its potential unknown being scanned with the primary electron beam 1, thereby obtaining an image of the mirror electrons 3. The potential on the sample 23 is obtained by comparing this image with the above reference images and performing computation.

In this embodiment, the charge quantity is detected by comparing the mesh image obtained by detecting the mirror electrons and a mesh image acquired in advance are compared to detect the displacement quantity between them, thereby detecting the quantity of charge. At that time, the potential on the sample can be measured by assigning the detected displacement quantity to an approximate function indicating the correlation between the displacement quantity and the potential on the sample.

At that time, it is desirable that an image that is the target for the comparison is an image obtained when the potential on the sample is 0 V in the sense of detecting the displacement quantity, but the present invention is not limited to this, and a displacement quantity from an image obtained when the sample potential is substantially 0 V may be obtained by, for example, comparing an image obtained when the potential on the sample is 100 V with the detected image.

Embodiment 3

Figure 4:
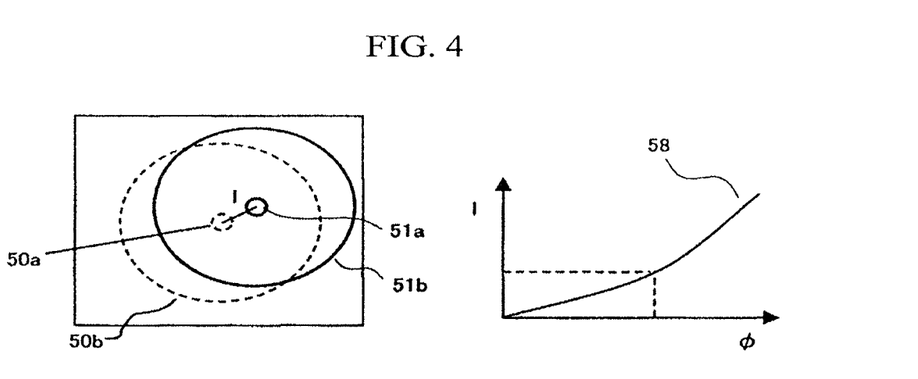
FIG. 4 is a diagram illustrating a method for detecting a displacement quantity of mirror electrons (Embodiment 3)

FIG. 4 is a diagram for describing a third embodiment for detecting the potential on a sample. From among reference images with their potentials known, for example, an image 50a for a beam transmission aperture, and an image 50b for a mesh are observed, while a sample 23 with its potential unknown is observed, and images (the beam transmission aperture image 51a, and the mesh image 51b) are acquired. The transfer distance 1 of the position of the hole is detected and the charge potential φ is obtained from a correlation curve prepared in advance. Here, the center of the hole is used for measuring the transfer distance, but a certain part of the mesh may also be used.

Embodiment 4

Figure 5:
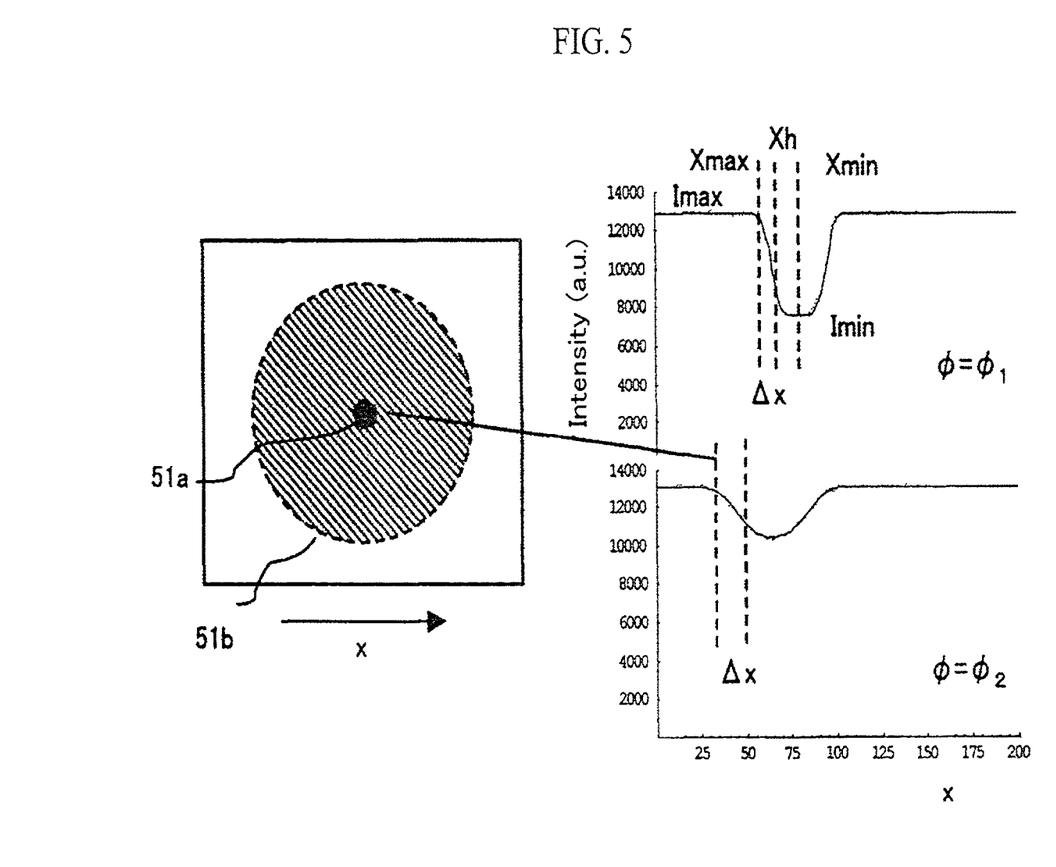
FIG. 5 is a diagram illustrating a method for detecting a displacement quantity of mirror electrons (Embodiment 4)

FIG. 5 is a diagram for describing a fourth embodiment for detecting the potential on a sample, and also for describing a method for calculating a displacement caused by charging. In this embodiment, a displacement is obtained from a change in distribution of luminance I of an image. Setting the direction traversing an image 51a of a beam transmission aperture to x, the distribution of luminance I in this direction is calculated. At that time, setting the intensity at an edge Xmax of the displayed hole to Imax, and the intensity at the center part Xmin of the hole to Imin, a position Xh at which the image intensity I is equal to (Imax+Imin)/2 is calculated. Defining Δx=|Xmax−Xh|, Δx is a half width.

This Δx is used as a value for determining a displacement quantity. Here, when the charge potential changes (the lower graph), the half width Δx also changes. The charge potential can be obtained by calculating the change in the half width Δx of the signal intensity using a detector 29 and a computing unit 40. Instead of the half width of the luminance, the radius of the hole displayed in an image 51a of a beam transmission aperture may also be used.

Embodiment 5

Figure 6:
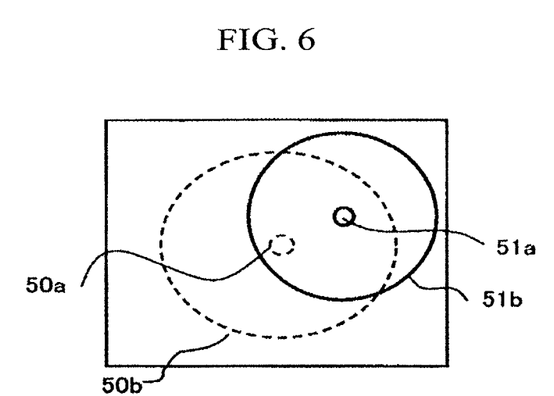
FIG. 6 is a diagram illustrating a method for detecting a displacement quantity of mirror electrons (Embodiment 5)

FIG. 6 is a diagram for describing a fifth embodiment for detecting the potential on a sample, and also for describing a method for calculating a displacement due to charging. As an index for the displacement, a change in area of an image is used. The area S0 of an image 50a of a beam transmission aperture or of a contour of an image 50b of a mesh in a reference image with its potential already known is obtained for each of various kinds of voltages that have been changed from one another.

An image formed by mirror electrons 3 is acquired by a sample 23 with its potential unknown being scanned with a primary electron beam 1. An area S1 of a hole within an image 51a of the beam transmission aperture or a contour of an image 51b of the mesh at that time is calculated. The potential on the sample 23 is obtained by comparing this area with S0 above by means of a computing unit 40 and performing computation.

Embodiment 6

Figure 7:
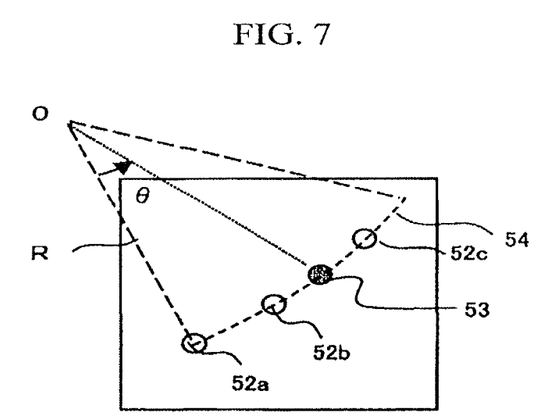
FIG. 7 a diagram illustrating a method for detecting a displacement quantity of mirror electrons (Embodiment 6)

FIG. 7 is a diagram for describing a sixth embodiment for detecting the potential of a sample, and also for describing a method for calculating a displacement due to charging. A rotation angle of an image is detected from a hole appearing in the image and an image of a position of a certain point of a structure. Several samples 23 with their potentials already known are prepared and an image by means of mirror electrons 3 is acquired. For example, changed positions 52a, 52b and 52c of a beam transmission aperture accompanying changes in the potential of the beam transmission aperture position 53 during potential measurement are acquired, and a curvature radius R and a center position O are obtained from a curve fitted to an orbit 54 of the beam transmission aperture position.

In the case of a sample with its charge potential unknown, the beam transmission aperture position 53 during the potential measurement performed by scanning is detected, and an angle θ is calculated from the changed position 52a of the beam transmission aperture accompanying a change in the potential of the beam transmission aperture position 53 during potential measurement.

Using a computing unit 40, the charge potential is calculated from the orbit 54 of the beam transmission aperture position corresponding to the angle θ. Here, the description has been given with regard to a hole through which a beam passes, but the calculation may be performed based on a change in an angle of an image of another structure.

Embodiment 7

Figure 8:
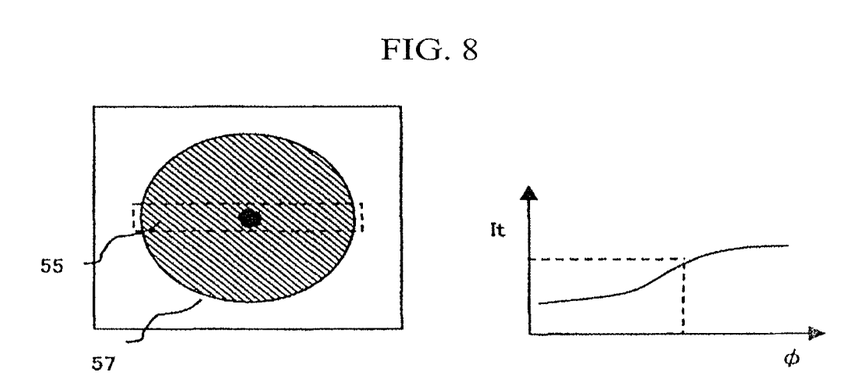
FIG. 8 a diagram illustrating a method for detecting a displacement quantity of mirror electrons (Embodiment 7)

FIG. 8 is a diagram for describing a seventh embodiment for detecting a potential on a sample, and also for describing a method for calculating a displacement due to charging. More specifically, it is a method for calculating a displacement from an incident position of mirror electrons 3 based on changes in luminance of a hole or structure appearing in an image.

Of an image 57 of a hole, the luminance of a certain portion 55 is integrated to calculate a luminance integration value It. Using the nature that the area and luminance of the certain portion 55 changes when the potential of a sample 23 changes, the charge potential of the sample is calculated from the size of It.

Embodiment 8

Figure 9:
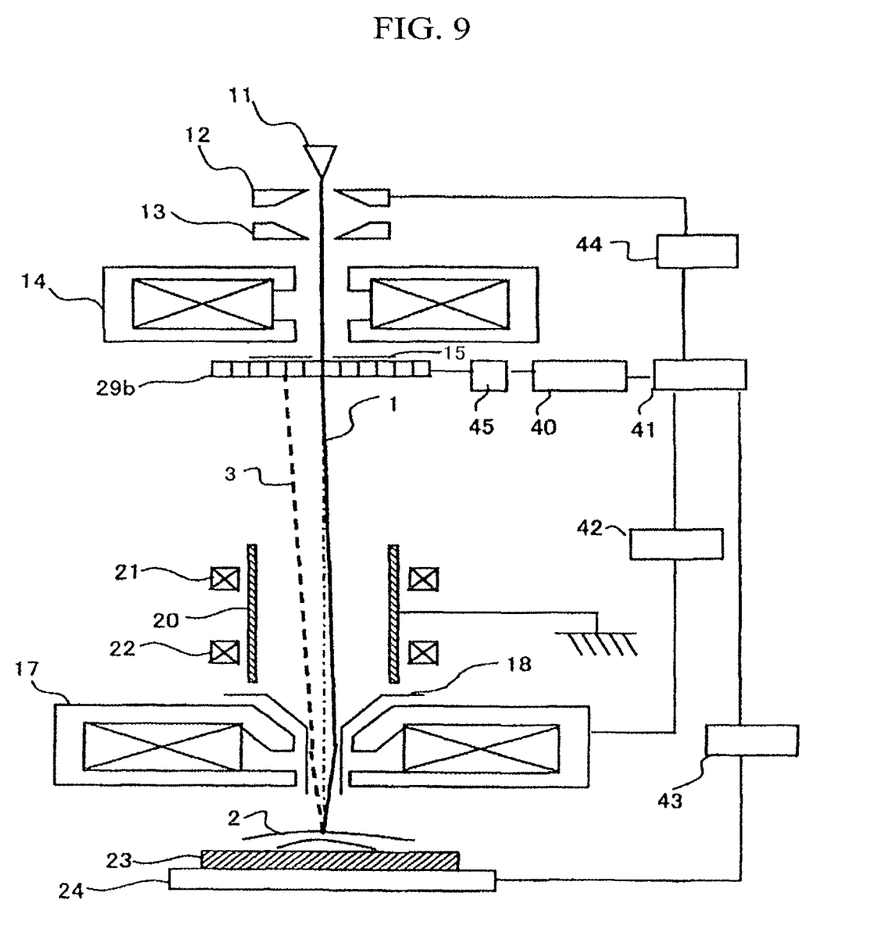
FIG. 9 is a still another scanning electron microscope configuration.

FIG. 9 is a diagram for describing an eighth embodiment for detecting a potential on a sample, and it is a schematic view of a scanning electron microscope for implementing a potential measurement method in this embodiment. A plurality of detectors 29b are placed at positions where mirror electrons 3 are detected to detect the positions where the mirror electrons 3 have arrived and the amount of the mirror electrons 3.

Figure 10:
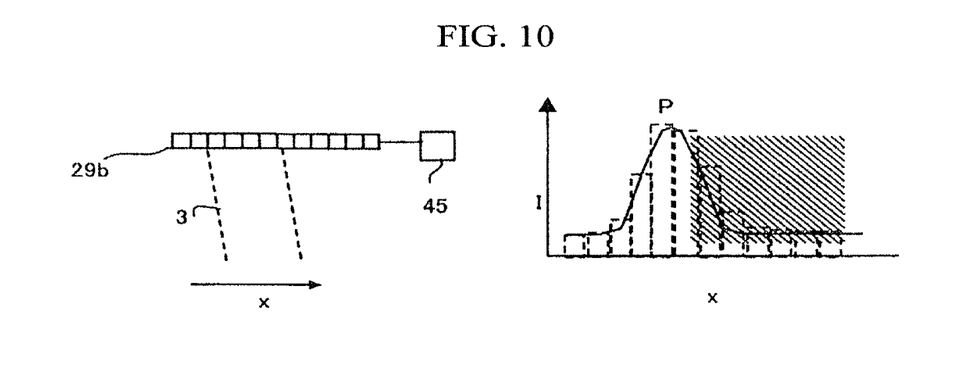
FIG. 10 is a diagram for illustrating an example of a method for forming a processed signal.

The detected signals are conveyed to a second computing unit 45, and addition/reduction for the signals, the detection of a peak position P, and filtering are performed, resulting in processed signal data (see FIG. 10). This signal is compared with a signal of a reference value and computed in a computing unit 40 to obtain the charge potential.

As described above, according to the preferred embodiments of the present invention, the quantity of charge can be measured without an electron beam reaching the sample, and accordingly, new charging will not be induced by electron beam application, so an accurate charge measurement can be achieved. Although the above-described embodiments have referred to an example in which a charge quantity is measured based on, for example, the relationship between the potential on the sample and the position where the mirror electrons have arrived, the present invention is not limited to this example, and it is also possible that a compensation value for another apparatus parameter to be adjusted is detected without measuring the charge quantity, by obtaining, in advance, the correlation between the position where the mirror electrons have arrived and that other apparatus parameter to be adjusted, for example.

The invention claimed is:

1. A method for measuring an electric potential on a sample, comprising determining the electric potential on the sample based on charged particles reflected without reaching the sample in a state in which a charged particle beam emitted from a charged particle source is applied toward the sample,
    wherein when a retarding voltage for decelerating the charged particle beam is greater than an acceleration voltage for accelerating the charged particle beam, information on an orbit of the charged particles is obtained based on charged particles detected by a charged particle detector placed between the charged particle source and an objective lens that focuses the charged particle beam, and
    an electric potential on the sample is determined by referring to data showing a correlation between the electric potential on the sample and a difference between the obtained information and information on an orbit of the charged particles detected by the charged particle detector at a predetermined electric potential on the sample.

2. The method for measuring an electric potential on a sample according to claim 1,
    wherein the information on the orbit of the charged particles relates to a position where charged particles reflected by an electric field formed by the retarding voltage without reaching the sample have reached the charged particle detector.

3. The method for measuring an electric potential on a sample according to claim 2, further comprising obtaining the electric potential on the sample based on a difference between the position where the charged particles have reached the charged particle detector, and a position where the charge particles have reached the charged particle detector that is obtained at the predetermined electric potential on the sample.

4. The method for measuring an electric potential on a sample according to claim 2, wherein the information on the position where the reflected charged particles have reached the charged particle detector relates to a spread or positions of the charged particles projected in the charged particle detector.

5. The method for measuring an electric potential on a sample according to claim 1, wherein the information on the orbit of the charged particles relates to an image formed based on charged particles reflected by an electric field formed by the retarding voltage without reaching the sample and detected by the charged particle detector.

6. The method for measuring an electric potential on a sample according to claim 5, further comprising obtaining the electric potential on the sample based on a difference in transfer quantity, blurring quantity and/or rotation quantity between the image formed based on the charged particles and an image obtained based on charged particles at the predetermined electric potential on the sample.

7. The method for measuring an electric potential on a sample according to claim 1, further comprising: obtaining a relationship between the predetermined electric potential on the sample and the information on the orbit of the charged particles detected by the charged particle detector at the predetermined electric potential on the sample; and determining the potential on the sample based on the obtained relationship.

8. A charged particle beam apparatus comprising:
a charged particle source;
an objective lens that focuses a charged particle beam emitted from the charged particle source;
a charged particle detector placed between the charged particle source and the objective lens;
a power source for applying a voltage for decelerating the charged particle beam to a sample; and
a controller that controls the voltage,
wherein the controller obtains information on an orbit of charged particles based on charged particles detected by the charged particle detector when a voltage higher than an acceleration voltage for accelerating a charged particle beam emitted from the charged particle source is applied to the sample in a state in which the charged particle beam is applied from the charged particle source toward the sample, and determines an electric potential on the sample by referring to data showing a correlation between the electric potential on the sample and a difference between the obtained information and information on an orbit of charged particles detected at a predetermined electric potential on the sample.

* * * * *